United States Patent [19]

Batorewicz et al.

[11] Patent Number: 4,479,008
[45] Date of Patent: Oct. 23, 1984

[54] PREPARATION OF P-NITROSODIPHENYLAMINE

[75] Inventors: Wadim Batorewicz, New Haven; Edward L. Wheeler, Watertown, both of Conn.

[73] Assignee: Uniroyal, Inc., New York, N.Y.

[21] Appl. No.: 430,104

[22] Filed: Sep. 30, 1982

[51] Int. Cl.³ .................. C07C 76/00; C07C 81/00
[52] U.S. Cl. .................................. 564/433; 564/410
[58] Field of Search ............................. 564/433, 410

[56] References Cited

U.S. PATENT DOCUMENTS

| | | | |
|---|---|---|---|
| 2,782,239 | 2/1957 | Lantz et al. ........................ | 564/410 |
| 3,248,362 | 7/1973 | Kinstler ........................ | 564/433 X |
| 3,340,302 | 9/1967 | Young ........................ | 564/433 X |
| 3,429,924 | 2/1969 | Ellerbrook et al. ................ | 564/410 |
| 4,034,042 | 7/1977 | Wedemeyer et al. ................ | 564/410 |
| 4,313,002 | 1/1982 | Symon et al. ................... | 564/410 X |
| 4,362,893 | 12/1982 | Kurek ............................ | 564/433 X |

Primary Examiner—Paul F. Shaver
Attorney, Agent, or Firm—Andrew D. Maslow

[57] ABSTRACT

A process for preparing p-nitrosodiphenylamine hydrochloride is provided from N-nitrosodiphenylamine and hydrogen chloride. The product is prepared in the absence of an aromatic solvent and using a solvent consisting essentially of aliphatic $C_5$–$C_{10}$ alcohol.

2 Claims, No Drawings

PREPARATION OF P-NITROSODIPHENYLAMINE

This invention relates to an improved process for the preparation of p-nitrosodiphenylamine (pNDPA) hydrochloride employing as a solvent a saturated aliphatic alcohol substantially immiscible with water.

In this process, a solution of N-nitrosodiphenylamine (NNDPA) is treated with an appropriate excess of hydrogen chloride, giving pNDPA hydrochloride slurry. The pNDPA hydrochloride slurry of the present process is unusually stable and can be kept for a prolonged period of time without significant deterioration. The pNDPA hydrochloride slurry may be neutralized with an aqueous base and pNDPA recovered.

The pNDPA can be hydrogenated without isolation from the solvent, if desired, to p-aminodiphenylamine, a known precursor for antiozonants, or reductively alkylated with an appropriate ketone to give the antiozonant directly.

The instability of the pNDPA hydrochloride reaction slurry in the processes employing an alcohol and an aromatic solvent systems is well known to those skilled in the art, and is sometimes referred to as gelation. On occasions, due to localized overheating and possibly other factors, rapid decomposition has been observed in such two-solvent systems during the preparation of pNDPA hydrochloride. The pNDPA hydrochloride slurry decomposes even at room temperature. If kept over a period of time, a gradual darkening of the brick-red mixture is noted, and the viscosity of the reaction mass increases to the point where the recovery of the undecomposed product is no longer practical. For this reason, once the reaction is completed, the reaction mass is neutralized as quickly as possible. This is a highly undesirable feature in any commercial process.

The state of the prior art has been summarized in U.S. Pat. No. 4,034,042. The shortcomings of the previously disclosed processes as related to the instability of the pNDPA hydrochloride reaction mass are discussed therein in some detail. The improvement claimed in U.S. Pat. No. 4,034,042 is that the pNDPA hydrochloride is kept in solution by substantially increasing the ratio of the alcohol, usually methanol to the aromatic hydrocarbon solvent. However, this solvent system does not stabilize pNDPA hydrochloride, but only moderates its decomposition so that the possibility of gelation is minimized. As a consequence, the reaction solution has to be neutralized as quick as possible to prevent serious yield losses. As disclosed in U.S. Pat. No. 4,034,042, FIG. 1, the pNDPA hydrochloride in solution is about 50% decomposed in about four hours at 40° C.

An object of this invention is to provide a process for the preparation of p-nitrosodiphenylamine in which only one solvent is used, namely an aliphatic alcohol essentially in the absence of an aromatic solvent, thereby decreasing the probability of decomposition of the product upon storage.

It is a further object of this invention to provide a process for the preparation of p-nitrosodiphenylamine in which there is a reduced loss of solvent.

The p-nitrosodiphenylamine made by the invention may be used as an intermediate in the preparation of N-phenyl-N'-substituted-p-phenylenediamines. For example, N-phenyl-N'-cyclohexyl-p-phenylenediamine and N-phenyl-N'-$C_3$ to $C$-secalkyl-p-phenylenediamines are effective antiozonants for use in rubber products.

In accordance with the invention N-nitrosodiphenylamine (NNDPA) may be prepared by nitrosation of diphenylamine (DPA) with nitrous acid. A mineral acid such as sulfuric acid is added incrementally to a stirred mixture of acqueous sodium nitrite and DPA. It is advantageous to employ an alphatic $C_5$–$C_{10}$ alcohol substantially immiscible with water as a solvent. The reaction takes place essentially in the absence of an aromatic solvent. The reaction product, NNDPA, is dissolved in said alcohol solvent and subsequently rearranged to p-nitrosodiphenylamine (pNDPA) hydrochloride by using an excess of hydrogen chloride. The resulting pNDPA slurry has an unexpectedly superior storage stability when compared to the slurries produced by the prior art processes.

In the nitrosation of DPA it is advantageous, but not essential, to employ an excess of nitrous acid which can range from about 0.1 to about 20 mole percent excess over the DPA. Normally, about 10 mole percent excess of nitrous acid is employed.

The temperature during the nitrosation step may be kept from about 10° C. to about 50° C. It is convenient, however, to keep the temperature in 30–40° C. range. At this temperature, NNDPA stays in solution, which facilitates the separation of the organic and aqueous phases at the end of the reaction.

The DPA-alcohol solution to be employed in the present process can range from about 10% to about 40% DPA by weight. However, a 20–25 solution of DPA is preferred. Starting at this concentration range, the pNDPA hydrochloride slurry produced in the next step was found to possess very good mixing and heat transfer properties and was easy to handle during subsequent work-up as well, with no sacrifice in productivity as is the case with more dilute solutions.

The NNDPA is rearranged to pNDPA hydrochloride in presence of an excess of hydrogen chloride, which is added sub-surface to a stirred solution of NNDPA in an alcohol. It is beneficial, but not essential to add hydrogen chloride at a fast rate commensurate with heat removal and then allow the reaction to proceed to completion. The addition time may vary from about one hour to about five hours, preferably from two to three hours. The reaction mass is then stirred from one to five hours or longer if necessary, depending on the hydrogen chloride addition rate, the excess of the acid used and the temperature employed.

The rearrangement leading to pNDPA hydrochloride is an exothermic reaction, so that cooling is required especially at the initial stage. This step can be carried out at temperatures ranging from about 20° C. to about 50° C., the preferred range is from about 30° C. to 35° C.

The presence of an excess of hydrogen chloride over NNDPA is necessary to drive the reaction to completion. The molar ratios of hydrogen chloride to NNDPA contemplated for the present process can vary from about 1.5:1 to 3.0:1. The preferred ratio being in the range from 2.0:1 to 2.2:1.

The saturated aliphatic alcohols useful as solvents for the present invention can be primary or secondary, linear or branched, having from $C_5$ to $C_{10}$ carbon atoms and having a boiling point in the range of about 130° C. to 200° C. Primary alcohols are preferred as a solvent for this process over the secondary alcohols because they are less prone to enter side reactions with hydrogen chloride, forming water and an alkyl chloride. A buildup of the alkyl chloride by-product in the solvent will necessitate, eventually, removal of such alkyl chloride from the alcohol. In addition, even a small loss of the alcohol due to this side reaction may adversely affect the economics on a commercial scale.

The preferred alcohols of the present invention are substantially immiscible with water. Small losses of the alcohol to the aqueous phase are economically unacceptable on a commercial scale and usually require a burdensome separation procedure for the recovery of the solvent.

The preferred alcohols of the present process are primary saturated aliphatic alcohols having from $C_6$ to $C_8$ carbon atoms. Examples of such alcohols are n-hexanol, n-octanol and 2-ethylhexanol. The most preferred alcohol is hexanol.

The presence of small amounts of water in the $C_5$–$C_{10}$ alcohol has been found not to be detrimental to pNDPA hydrochloride stability.

When the reaction is completed, the pNDPA slurry may be treated with an inorganic base, usually sodium hydroxide, to a pH from about 7 to about 14. It is preferred to stop the addition of the base when the pH of the mixture reaches a value of from about 8 to about 9. The mixture is heated to 70° C.–80° C. at which point essentially all of pNDPA is in solution in the alcohol. If necessary, the pH of the mixture is adjusted again to an 8 to 9 value with addition of more base. The aqueous phase is discarded, the alcohol phase is cooled and pNDPA is recovered by crystallization.

EXAMPLE 1

Preparation of p-Nitrosodiphenylamine

To a 2-liter resin flask, fitted with a mechanical stirrer, a thermometer, and air gas inlet tube was charged hexanol (676 g), DPA (169 g, 1.0 mole) and sodium nitrite solution (76.0 g, 1.1 moles dissolved in 116 g of water). Sulfuric acid solution (59.5 g of 96% $H_2SO_4$ dissolved in 110 g of water) was added dropwise to the stirred mixture over a 30 minute period. The temperature of the reaction mixture was allowed to rise to 40° C. and held at this temperature for 15 minutes after the completion of the acid addition. The aqueous bottom layer was separated and discarded. The temperature of the hexanol layer, now containing N-nitrosodiphenylamine, was adjusted to 30°–35° C., and hydrogen chloride (80.3 g, 2.2 moles) was added sub-surface through the gas inlet tube, while stirring and cooling the reaction mass by means of an ice-water bath. It took about two hours to complete HCl addition, during which a brick-red precipitate of pNDPA hydrochloride separated. The resulting slurry was stirred for four hours at about 30°–35° C., then treated dropwise with a 14% solution of sodium hydroxide. The exotherm of neutralization was controlled by an ice-water bath so that the temperature of the reaction mass was not allowed to rise above about 45°–50° C. The addition of sodium hydroxide was stopped when the pH of the mixture reached a value of between 8 and 9. The mixture was stirred at about 40°–50° C. for 30 minutes, then heated to 75°–80° C., during which time the pH dropped below 7. The pH was adjusted back to about 8.5 by the addition of sodium hydroxide solution. While keeping the temperature at 75°–80° C., the aqueous phase was separated and discarded. The hexanol phase was kept overnight at about 5° C. and the bluish-black crystals of pNDPA were separated by filtration, washed with hexane and air-dried at 60° C. overnight. Recovered 185 g of pNDPA, m.p. 142°–144° C., 93% yield based DPA.

EXAMPLE 2

This example shows the stability of the pNDPA slurry of Example 1.

The procedure of Example 1 was repeated but using one half as much of each component. The resulting pNDPA hydrochloride slurry was then kept at about 30° C. for 72 hours, after which, the pNDPA was recovered by the procedure described in Example 1. Recovered 92.0 g of pNDPA, m.p. 138°–142° C., 93% yield based on DPA.

EXAMPLE 3

Preparation of p-Aminodiphenylamine pNDPA was prepared according to the procedure described in Example 1, except that one half as much of each component was used and the product was not isolated from the alcohol solvent. The neutralized slurry was charged to a 1-liter autoclave and hydrogenated over a 5% Pd/C catalyst (0.15 g) at a hydrogen pressure of from 500 to 800 psi at 80° C. After about 30 minutes, the autoclave was cooled and the hexanol solution filtered to remove the catalyst and washed with water (2×300 ml). Hexanol and p-aminodiphenylamine were recovered by vacuum distillation. Collected 79 g of p-aminodiphenylamine which solidified to a light tan mass on cooling, m.p. 70°–72° C., 85.9% yield based on DPA.

EXAMPLE 4

The procedure of Example 1 was repeated except that pentanol was used instead of hexanol. The yield pNDPA was 92.9%, m.p. 141°–144° C.

EXAMPLE 5

The procedure of Example 1 was repeated except that 2-Ethylhexanol was used instead of hexanol. The yield pNDPA was 98.6%, m.p. 141°–144° C.

EXAMPLE 6

The procedure of Example 1 was repeated except that the HCl/DPA molar ratio was reduced to 1.5/1 and the reaction temperature was raised to 50° C. The yield of pNDPA was 58%, m.p. 132°–140° C.

EXAMPLE 7

The procedure of Example 1 was repeated except that the temperature was raised to 40° C. The yield of pNDPA was 80.3%, m.p. 139°–143° C.

EXAMPLE 8

The procedure of Example 1 was repeated except that 1-pentanol was used instead of 1-hexanol, the HCl/DPA molar ratio was raised to 2.5/1 and the temperature was lowered to 20° C. The yield of pNDPA was 60%, m.p. 138°–141° C.

EXAMPLE 9

The procedure of Example 1 was repeated except that the HCl addition period was extended to 4 hours then the mixture was stirred for one hour. The yield of pNDPA was 84%, m.p. 141°–144° C.

What is claimed is:

1. An improved process for preparing p-nitrosodiphenylamine hydrochloride from N-nitrosodiphenylamine and hydrogen chloride, the improvement comprising carrying out said process in the presence of a $C_5-C_{10}$ saturated aliphatic alcohol essentially in the absence of an aromatic solvent;

wherein said N-nitrosodiphenylamine is prepared by contacting diphenylamine with sodium nitrite and dilute sulfuric acid in the presence of a $C_5-C_{10}$ saturated aliphatic alcohol essentially in the absence of an aromatic solvent; and further comprising contacting said diphenylamine with from 0.1 to 20 mol percent nitrous acid in excess over the amount of said diphenylamine.

2. A process according to claim 1 wherein the temperature of the reaction preparing the N-nitrosodiphenylamine is kept in the 30°–40° C. range and the diphenylamine-alcohol solution ranges from 10% to 40% diphenylamine by weight.

* * * * *